US011690790B2

(12) United States Patent
Keeton

(10) Patent No.: US 11,690,790 B2
(45) Date of Patent: Jul. 4, 2023

(54) MEDICAL DEVICE SOLUTIONS FOR TREATING DENTAL DISEASE AND METHODS FOR THE TREATMENT OF DENTAL DISEASE

(71) Applicant: Kytodent, LLC, Boerne, TX (US)

(72) Inventor: David Keeton, Boerne, TX (US)

(73) Assignee: Kyodent, LLC, Boerne, TX (US)

( * ) Notice: Subject to any disclaimer, the term of this patent is extended or adjusted under 35 U.S.C. 154(b) by 0 days.

(21) Appl. No.: 16/924,647

(22) Filed: Jul. 9, 2020

(65) Prior Publication Data
US 2021/0007947 A1 Jan. 14, 2021

Related U.S. Application Data

(60) Provisional application No. 62/872,460, filed on Jul. 10, 2019.

(51) Int. Cl.
| | | |
|---|---|---|
| A61K 8/04 | (2006.01) | |
| A61K 8/73 | (2006.01) | |
| A61K 8/21 | (2006.01) | |
| A61K 33/38 | (2006.01) | |
| A61K 6/20 | (2020.01) | |
| B82Y 30/00 | (2011.01) | |
| B82Y 5/00 | (2011.01) | |
| A61K 9/06 | (2006.01) | |

(52) U.S. Cl.
CPC ............... *A61K 8/042* (2013.01); *A61K 6/20* (2020.01); *A61K 8/21* (2013.01); *A61K 8/736* (2013.01); *A61K 33/38* (2013.01); *A61K 9/06* (2013.01); *A61K 2800/74* (2013.01); *A61K 2800/87* (2013.01); *B82Y 5/00* (2013.01); *B82Y 30/00* (2013.01)

(58) Field of Classification Search
CPC ...... A61Q 11/00; A61K 8/0241; A61K 33/38; A61K 8/21; A61K 6/844; A61K 8/736; A61K 6/20; A61K 8/042; A61K 9/06; A61K 2800/413; A61K 9/5161; A61K 2800/87; A61K 2800/74; B82Y 30/00; B82Y 5/00
See application file for complete search history.

(56) References Cited

U.S. PATENT DOCUMENTS

| | | |
|---|---|---|
| 2003/0194381 A1 | 10/2003 | Galli |
| 2011/0014258 A1 | 1/2011 | Gan et al. |
| 2017/0007737 A1* | 1/2017 | Moradian-Oldak ......... A61L 27/446 |
| 2017/0197070 A1* | 7/2017 | Masri ..................... A61K 41/00 |

FOREIGN PATENT DOCUMENTS

| | | | |
|---|---|---|---|
| CN | 107569395 A | | 1/2018 |
| TR | 201608805 | * | 8/2016 |

OTHER PUBLICATIONS

Craig et al. "Clinical evaluation of diamine silver fluoride? potassium iodide as a dentine desensitizing agent. A pilot study" Australian Dental Journal, vol. 57 Issue 3 (Sep. 2012): pp. 308-311; abstract, p. 308 col. 2 para 2-para 3, p. 309 col. 1 para 5, p. 309 col. 2 para 3, p. 310 col. 2 para 5.
Toledano et al. "Zn-containing polymer nanogels promote cervical dentin remineralization" Clinical Oral Investigations, vol. 23 (Jul. 3, 2018): entire document, but especially: pp. 1197-1208; p. 5 para 3, p. 5 para 4, p. 6 para 1, p. 6 para 3, p. 14 para 1.
Oktavia et al. "Potency of Chitosan Nano Gel as Desensitizing Agent" Proceeding International Scientific Meeting (TINI IV) & Ikorgi National Congress XI (Nov. 3-5, 2017): pp. 389-397; abstract, p. 395 col. 1 para1, p. 397 col. 1 para 3.
Toledano-Osorio et al. "Improved reactive nanoparticles to treat dentin hypersensitivity" Acta Biomaterialia, vol. 72 (Mar. 24, 2018): pp. 371-380; entire document.
Song et al. "Nanogels of carboxymethyl chitosan and lysozyme encapsulated amorphous calcium phosphate to occlude dentinal tubules" Journal of Materials Science: Materials in Medicine, vol. 29 Article 84 (Jun. 11, 2018): pp. 1-11.
International Search Report and Written Opinion received for International Application No. PCT/US20/41360 dated Oct. 16, 2020, 14 pages.

* cited by examiner

*Primary Examiner* — Lezah Roberts
(74) *Attorney, Agent, or Firm* — Bernard G. Pike; Pike IP Law, PLLC

(57) ABSTRACT

A medical device or solution for treating dental discomfort by at least partially occluding dental tubules is disclosed. The medical device or solution contains a polysaccharide or other biocompatible polymer with an antimicrobial metal, antimicrobial metal compound, or antimicrobial metal ion bound to a biopolymer. The medical device or solution further comprises at least one soluble antimicrobial. The soluble antimicrobial may be a water soluble metal iodide, water soluble metal fluoride, or a water soluble metal chloride encompassed with the nanogel. The medical device may be a solution of a chitosan with a nanoparticle of silver fluoride on the chitosan and at least one of a sodium fluoride or silver fluoride. The solution may be water based solution. Methods of applying the medical device or solution are also disclosed.

9 Claims, No Drawings

MEDICAL DEVICE SOLUTIONS FOR TREATING DENTAL DISEASE AND METHODS FOR THE TREATMENT OF DENTAL DISEASE

FIELD OF THE INVENTION

The invention relates generally to medical device and method for the treatment of dental disease and dentinal tubules.

BACKGROUND

Currently there are a number of solutions for treating dental disease and caries. Some of these solutions attempt to remove the bacteria physically and insert a filling material such as a resin composite into the weakened tooth structure, but these solutions fail to meet the needs of the industry because they are painful, expensive, and are treating a biochemical disease with mechanical methods.

Other solutions attempt to use fluoride supplements to convert hydroxyapatite to fluorapatite, but these solutions are similarly unable to meet the needs of the industry because they aren't sufficiently bactericidal and don't have a prolonged effect. Still other solutions seek to use silver diamine fluoride, but these solutions also fail to meet industry needs because it requires a great deal of silver ions, stains the teeth and mucosa black, has an offensive taste, and has a pH well above neutral causing a burning sensation in the patient's mouth.

SUMMARY OF THE INVENTION

It is desirable to have a medical device or solution that can sufficiently kill and inhibit the bacterial growth which may cause dental disease, and which can be safely applied. Furthermore, it would also be desirable to have a device that is easily applied. Still further, it would be desirable to have a device that occludes dentinal tubules to reduce sensitivity. Still further, it would be desirable to have a medical device or solution that remineralizes enamel and dentin of the tooth to prevent further decay. The disclosed medical device and solutions and associated method advantageously fill these needs and addresses the aforementioned deficiencies by providing a solution to kill and inhibit bacterial growth while simultaneously sealing and repairing the tooth.

The invention is directed to a medical device or solution for occluding a dentinal tubule. Teeth are not a solid piece of body tissue. Rather, teeth are comprised of layers of tissues that each serve unique functions. One of these layers, dentin, lies right under an enamel surface covering of the tooth. Tubules are present in normal teeth that pass through the dentin to help a person feel sensation in their teeth. While they are a part of normal tooth function, issues can arise.

Dentinal tubules are microscopic channels that radiate from the underside of the enamel surface to the inside pulp of the tooth. Dentin is the major structural component and middle layer of the tooth, supporting the brittle enamel on the exterior surface. Dentin is less mineralized than the enamel and forms the bulk of the tooth.

These small, hollow canals, tubules, in the dentin can convey sensations from the outside of the tooth to the inside. This sensitivity can be uncomfortable for patients if the enamel surface is worn down or otherwise thinned exposing the dentin to more stimuli. The tubules may transmit hot and cold sensation and sticky and acidic stimuli through the tooth. This stimulates the nerves and cells inside the tooth, causing discomfort.

These exposed or overstimulated dentinal tubules may be occluded to reduce the discomfort in a patient. Embodiments of the medical device or solution may be applied to the tooth to occlude the dentinal tubule. In one embodiment, the medical device or solution may comprise a nanogel or other polymer to carry an antimicrobial into the dentinal tubule to kill microbes and at least partially seal the dentinal tubule to ease discomfort.

In another embodiment, the medical device or solution may comprise a polysaccharide or other biocompatible polymer; an antimicrobial metal, antimicrobial metal compound, or antimicrobial metal ion bound to the polysaccharide or other biocompatible polymer. The medical device may further comprise at least one of a water soluble metal iodide, water soluble metal fluoride, and water soluble metal chloride encompassed within the nanogel or polymer.

The polysaccharide may include, but is not limited to, chitosan, dextran, or other low molecular weight polysaccharide. The polysaccharide may be a copolymer comprising a polysaccharide. In one embodiment, the chitosan, dextran, nanogel, or other biocompatible polymer may have a molecular weight in the range of 50,000 to 200,000 Da. The polysaccharide, chitosan, dextran or other biocompatible polymer may be modified to change its properties, if desired. In some embodiments, the biocompatible polymers may be functionalized or otherwise reacted to change the water solubility of the biocompatible polymer. For example, such biocompatible polymers may be deacetylated, such as, but not limited to, at least partially deacetylated chitosan, for example. The degree of deacetylation, in chitosan, for example, may be greater than 75%. Chitosan may be water insoluble be made to be water soluble by being deacetylated, for example.

The antimicrobial metal, antimicrobial metal compound, or antimicrobial metal ion may comprise silver, copper, or zinc, for example.

The water soluble metal iodide, water soluble metal fluoride, and water soluble metal chloride may comprise, but not limited to, a water soluble silver compound such as silver fluoride and silver diamine fluoride, or sodium fluoride, for example.

The antimicrobial metal, antimicrobial metal compound, or antimicrobial metal ion may have a diameter of less than 100 nm to facilitate travel and deposition within the dentinal tubule.

Embodiments of the method of the invention may be directed to a method of occluding dentinal tubules. One such embodiment of the method of occluding dentinal tubules in a tooth comprises applying an amount of a medical device or solution describe herein to a treatment area of the at least one tooth. The method may further comprise drying the tooth and/or applying a covering agent over the treatment area of the tooth.

Therefore, an embodiment of the method of occluding dentinal tubules in a tooth comprises drying at least one tooth, applying an effective amount of a medical device or solution to a treatment area of the at least one tooth. The medical device or solution may comprise a solution comprising a polysaccharide or other biocompatible polymer, an antimicrobial metal or metal ion bound to the polysaccharide or other biocompatible polymer, and an antimicrobial metal fluoride encompassed within the nanoparticle gel, and applying a covering agent over the treatment area of the tooth.

Drying the at least one tooth may also comprise desiccating at least one dentinal tubule to form a desiccated tubule. The polysaccharide or other biocompatible polymer may bind to bacteria within the desiccated tubule to deliver the antimicrobial and other components of the medical device. An antimicrobial metal fluoride in the medical device or solution (silver fluoride, for example) may form a fluorapatite when binding within the tooth to at least partially occlude a dentinal tubule.

In one embodiment, the medical device comprises a biocompatible polymer (biopolymer) and a metal bound to the biopolymer. The medical device may further comprise a solution for the biopolymer. In some further embodiments, a fluoride or a fluoride containing compound may also be bound to the biopolymer or in solution with the biopolymer. The metal and/or the fluoride may be bound to the biopolymer by any chemical bonding or caged in a polymer matrix, for example. The chemical bonding may be covalent, ionic, hydrogen bonding or van der Waal forces. The metal may have antimicrobial properties and more specifically a metal that has antimicrobial properties toward microbes that are detrimental to dental health.

The antimicrobial metal may include metal ions selected from the group comprising silver ions, copper ions, zinc ions or a combination thereof, as antimicrobial metal ions and/or a metal selected from the group comprising silver, copper, zinc, or a combination thereof, as an antimicrobial metal in a metal state.

Some microbes that are detrimental to oral health. In some embodiments, the biopolymer is capable of binding to the surface of the cell walls of gram negative or gram positive bacteria.

The biopolymer may be a biocompatible polymer. The biocompatible polymer may be a carbohydrate. The carbohydrate may be a natural or synthetic carbohydrate. The carbohydrate may be modified with the addition of functionality that more effectively bind to bacterial cell walls. For example, the polymer may comprise functional groups that attached to bacterial cell walls to more effectively deliver the antimicrobial metal to the bacteria. The biocompatible polymer can be sized such that the biopolymer and/or the solution may be drawn into a dentinal tubule. The biocompatible polymer may be a biodegradable polymer. In one embodiment, the biopolymer is chitosan. Chitosan is a deacetylated product of chitin. Chitosan has been found to have antimicrobial activity without toxicity to humans. Chitosan has been derived from the outer skeletons of crustaceans, mollusks, insects, and fungi. In a preferred embodiment, the chitosan is derived from fungal sources. The medical device may comprise other polysaccharides and/or functionalized or defunctionalized polysaccharides.

Disclosed may be a device and method for treating dental disease, which is made up of the following components metal, biopolymer, and fluoride. These components are connected in a liquid suspension as follows the metal is bound to biopolymer covalently and on a different amino group fluoride may be covalently bonded. These components in solution can be applied to an area of dental disease to kill or inhibit bacteria, remineralize the dentin and/or the enamel of the tooth, and occlude exposed dentinal tubules.

The device may also have one or more of the following: (1) the metals or metal ions, the metals or metal ions may be nanoscale particles, (2) multiple metals or metal ions bound to the biopolymer, (3) the biopolymer may be capable of biodegrading, (4) the fluoride or fluoride compound may or may not be bound to the biopolymer, for example, the fluoride may instead in the solution or not present at all.

Embodiments of a method may comprise the associated method may also include one or more of the following steps: (1) the substances may be bound by metallic, covalent or ionic bonds, (2) the solution may be water based, (3) the solution may be activated by physical, thermal or chemical means to promote biopolymer-metal bonding, and/or (4) the solution may be applied using a brush to areas of dental disease or hypersensitivity.

The disclosed device is unique when compared with other known devices and solutions because it provides: (1) bactericidal activity at low concentrations; (2) chemical complexes at nanoscale proportions; and (3) biopolymer bound and/or free molecules of fluoride. Similarly, the associated method is unique in that it: (1) is minimally invasive; (2) cost-effective; and (3) easily applied. Similarly, the disclosed method is unique when compared with other known processes and solutions in that it: (1) doesn't significantly stain teeth or tissues; (2) doesn't cause an uncomfortable burning sensation; and (3) binds within the dentinal tubules and partially biodegrades providing a sustained release of silver and fluoride.

The disclosed device is unique in that it is structurally different from other known devices or solutions. More specifically, in one embodiment, the device comprises: (1) nano-silver and fluoride bound to low-molecular weight chitosan; and (2) unbound sodium fluoride (NaF). These components may be any effective concentration in the liquid solution or suspension to occlude a dentinal tubule and reduce tooth sensitivity.

In one embodiment, the components (as measured in parts per million in the liquid) may be in a ratio of fluoride ion:chitosan:nanosilver of the ratio of 20:10:1. For example, in one embodiment, the components may be 44,000 ppm fluoride (4.4 wt. %), 20,000 ppm chitosan (2.0 wt %), 2,000 ppm nanosilver (0.2 wt. %) in the liquid suspension or solution. More generally, the ratio of components may be fluoride ion:Chitosan may be 0.5-4.0:1 and fluoride ion: nanosilver 5-40:1.

An embodiment of the medical device or solution comprises a solvent, a biopolymer in a range of 0.1 wt. % to the weight percent of solubility limit of the biopolymer in the solvent, nanosilver in a range of 0.05 wt % to the weight percent of the solubility of the biopolymer in the solvent; and 0.01 wt % to 0.5 wt % of fluoride ion.

Another embodiment of the medical device or solution comprises a solvent, a biopolymer in a range of 0.1 wt. % to the 10 wt. %; nanosilver in a range of 0.05 wt % to 6 wt. %; and fluoride ion in a range of 0.01 wt % to 0.5 wt %. In these embodiments, the nanosilver may be bound to the biopolymer. Also in these embodiments, the biopolymer may be a deacylated chitosan.

Furthermore, the process associated with the aforementioned device is likewise unique. More specifically, the disclosed process owes its uniqueness to the fact that it: (1) the chitosan used may be purified or reacted to be a chitosan polymer having a lower molecular weight and a high degree of deacetylation; (2) fluoride and nanospheres or other nanoparticles of silver are added in less than equal concentrations to chitosan and bound via methods known to the arts; and (3) sodium fluoride (NaF) is added in less than equal concentration to the previously formed molecule while titrating for neutral pH.

The embodiments of the described methods and the medical devices and solutions are not limited to the embodiments, components, method steps, and materials disclosed herein as such components, process steps, and materials may vary. Moreover, the terminology employed herein is used to describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be affected within the scope of the invention as defined in the appended claims. Accordingly, the scope of the various embodiments of the present invention should not be limited to the above discussed embodiments and should only be defined by the following claims and all equivalents.

This disclosure will now provide a more detailed and specific description that will refer to the accompanying drawings. The drawings and specific descriptions of the drawings, as well as any specific or alternative embodiments discussed, are intended to be read in conjunction with the entirety of this disclosure. The Medical device and method for the treatment of dental disease may, however, be embodied in many different forms and should not be construed as being limited to the embodiments set forth herein; rather, these embodiments are provided by way of illustration only and so that this disclosure will be thorough, complete and fully convey understanding to those skilled in the art.

DETAILED DESCRIPTION

The present invention is directed to a medical device or a solution and method for the treatment of dental disease. In one embodiment, the medical device or solution comprises nanospheres or other nanoparticles comprising a biocompatible polymer and silver or other antimicrobial metal. The medical device may be applied to a tooth comprising dentinal tubules. The exposed dentinal tubules may be causing discomfort due to enamel wear, decay, or other thinning of the enamel. The medical device or solution is capable of being drawn into the dentinal tubule by the application of pressure or capillary action, for example. Within the tubule, the biocompatible polymer may attach to any bacteria or other microbes and the silver or other antimicrobial metal carried on the biocompatible polymer within the tubule may then kill the bacteria or microbe.

It is desirable to have a medical device or a solution that may be applied to a tooth that can easily kill and inhibit bacteria which cause dental disease and to occlude dentinal tubules. The disclosed medical device or solution and associated method of applying the medical device or solution advantageously provides a solution to kill and inhibit bacteria while simultaneously at least partially sealing the dentinal tubule and repairing the tooth.

As such, the invention is directed to a medical device or solution for occluding a dentinal tubule. Dentinal tubules are microscopic channels that extend from the enamel surface of a tooth to the inside pulp. Dentin is the major structural component and middle layer of the tooth and supports the brittle enamel on the exterior surface of the tooth.

These small, hollow dentinal tubules through the dentin facilitate conveyance of sensations from the outside of the tooth to the inside toward the nerve. However, if the enamel is eroded or thinned, these sensations may be increased, and the sensitivity of the tooth can be uncomfortable or cause discomfort to a person.

To reduce the discomfort, the exposed dentinal tubules may need to be occluded. As described herein, a medical device or solution may be applied to the tooth to occlude the dentinal tubule. In one embodiment, the medical device or solution may comprise a nanogel, nanoparticle or other polymer carrier to deliver an antimicrobial into the dentinal tubule to kill microbes and also seal dentinal tubule to ease discomfort.

An embodiment of the medical device or solution for treating and occluding dentinal tubules comprises a nanoparticle comprising chitosan and a silver nanoparticle bound to the chitosan. Further incorporated in the nanoparticle may be a silver fluoride. Fluoride ions can react with free calcium ions to form deposits of calcium fluoride that can block dentinal tubules. The medical device may be drawn into a dental tubule by capillary action, wherein the chitosan may attach to any bacteria or microbes within the tubule and the antimicrobial silver nanoparticle and/or the silver fluoride may kill the bacteria or other microbe. The fluoride ions may then react with the calcium to form deposits within the dentinal tubule. Additionally, the nanoparticles may also remain in the tubule to occlude the tubule and reduce discomfort. In an embodiment, all the active components of the medical device or solution may be water soluble and the medical device or solution is a water based solution.

In another embodiment, the medical device or solution may comprise a polysaccharide or other biocompatible polymer; an antimicrobial metal, antimicrobial metal compound, or antimicrobial metal ion nanoparticle bound to the polysaccharide or other biocompatible polymer. The medical device may further comprise at least one of a water soluble metal iodide, water soluble metal fluoride, and water soluble metal chloride encompassed within the nanogel or polymer.

Biocompatible Polymers

The polysaccharide may include, but is not limited to, chitosan, dextran, or other low molecular weight polysaccharide. The polysaccharide may be a copolymer comprising a polysaccharide. The chitosan, dextran, nanogel, or other biocompatible polymer may have a molecular weight from 50,000-200,000 Da. The polysaccharide, chitosan, dextran, or other biocompatible polymer may be modified. For example, such polymers may be at least partially deacetylated, such as, but not limited to, an at least partially deacetylated chitosan.

A biocompatible polymer is a polymer that does not produce toxin or harmful products to human body or cells or stimulates an immune response in biological systems. This is preferred so that during implantation, the material does not induce a rejection response. The biocompatible polymers include, but are not limited to, polysaccharides, chitosan, dextran, modified polysaccharides, modified chitosan, modified dextran, copolymers thereof, and combinations thereof. The biocompatible polymers may be low molecular weight polymers, such as, having a molecular weight less than 200,000 daltons, or greater than 20,000 Daltons and less than 200,000. Such low molecular weight biocompatible polymers will more easily be deposited within the dentinal tubule. For example, the polymer may be a low molecular weight chitosan with a molecular weight more than 20,000 Daltons and less than 200,000 daltons.

The term "polysaccharide" further includes polysaccharides that have been modified by a reaction of its hydroxyl groups or other group with a compound to a different pendent functional group. The biopolymer may be a biodegradable polysaccharide. As used herein, "biodegradable polysaccharides" are polysaccharides that are biodegradable by enzymes present in a human. Additionally, the polysaccharide hydroxyl groups provide a vehicle for producing "tunable" hydrogels.

In some embodiments, the polysaccharide may be a polysaccharide of D-glucose monomers, linked by glycosidic bonds. Glucans include the following: dextran ($\alpha$-1,6-glucan with $\alpha$-1,3-branches); glycogen ($\alpha$-1,4- and $\alpha$-1,6-glucan); pullulan ($\alpha$-1,4- and $\alpha$-1,6-glucan); starch ($\alpha$-1,4- and $\alpha$-1,6-glucan); cellulose ($\beta$-1,4-glucan); chrysolaminarin ($\beta$-1,3-glucan); curdlan ($\beta$-1,3-glucan); laminarin ($\beta$-1,3- and $\beta$-1,6-glucan); lentinan (a strictly purified $\beta$-1,6:$\beta$-1,3-glucan from Lentinus edodes); lichenin ($\beta$-1,3- and $\beta$-1,4-glucan); oat beta-glucan ($\beta$-1,3- and $\beta$-1,4-glucan); pleuran ($\beta$-1,3- and $\beta$-1,6-glucan isolated from Pleurotus ostreatus); and zymosan ($\beta$-1,3-glucan). Other biodegradable/biocompatible polysaccharides include chitosan, which is a linear polysaccharide composed of randomly distributed $\beta$-(1-4)-linked D-glucosamine and N-acetyl-D-glucosamine, and hyaluronic acid. Hyaluronic acid is a polymer of disaccharides, themselves composed of D-glucuronic acid and D-N-acetylglucosamine, linked via alternating $\beta$-1,4 and $\beta$-1,3 glycosidic bonds.

In some embodiments comprising nanospheres or other nanoparticles, the nanospheres or other nanoparticles have a diameter of greater than 1 nm and less than 100 nm.

The biocompatible polymer, for example, chitosan, dextran or derivative thereof, may decompose within the dentinal tubule to deposit the other components within the tubule to facilitate its occlusion.

Antimicrobial Metal Nanoparticles

The medical device of solution may comprise an antimicrobial metal nanosphere or nanoparticle bound to the biocompatible polymer. The antimicrobial metal nanoparticle may be any particle that may kill or retard growth any bacteria or other microbe within the dental complex or a dentinal tubule and may occlude the tubule to prevent further discomfort in the patient.

The antimicrobial metal nanosphere or nanoparticle may comprise metal ions selected from the group comprising silver ions, copper ions, zinc ions or a combination thereof, as antimicrobial metal ions and/or a metal selected from the group comprising silver, copper, zinc, or a combination thereof.

In certain embodiments, the medical device or solution may comprise metal fluoride or other fluoride (such as, for example, silver fluoride) bound to biocompatible polymer in a 40:60 to 60:40 ratio, for example. In such an embodiment the biocompatible polymer may be chitosan and the fluoride may be silver fluoride, for example. The antimicrobial metal fluoride may form a fluorapatite when binding with the tooth to occlude the dentinal tubule.

Additional Antimicrobial

The medical device may comprise an additional antimicrobial that is not bound to the biocompatible polymer.

For example, fluoride bound to sodium or silver, in the form of sodium fluoride (NaF) or silver fluoride (AgF) may be encompassed within the nanogel or nanoparticle. In certain embodiments, the additional fluoride may be in approximately equal concentration to the chitosan. The components may be any effective concentration in the liquid solution or suspension. In one embodiment, the components (as measured in parts per million in the liquid) may be in a ratio of fluoride ion:Chitosan:nanosilver of about 20:about 10:about 1. For example, in one embodiment, the components may be 44,000 ppm fluoride, 20,000 ppm chitosan, 2,000 ppm nanosilver in the liquid suspension or solution. More generally, the ratio of components may be fluoride ion:Chitosan may be between 0.5 and 4.0:1 (or between 1 and 3:1, for example) and fluoride ion:nanosilver may be between 5 and 40:1 (or between 10 and 30:1, for example).

These components may be bound together chemically as follows by any chemical, thermal, electrical or through any type of irradiation. It should further be noted that, the components are suspended in a liquid suspension. Preferably the medical device or solution may be buffered to a pH of approximately neutral (5.5 to 7.5) and having a total concentration of active ingredients of 2 wt. % to 30 wt. %. The bound silver may resist oxidization and, therefore, no color, change would occur with the application of the medical device or solution to the tooth or in the oral cavity.

An embodiment of performing the method associated with the disclosed device comprise the following steps: isolating and drying of the tooth, using a microbrush to apply a drop of the disclosed solution to the affected area, applying a covering agent over the affected area. It should further be noted that: the drying of the tooth dessicates dentinal tubules, that the disclosed invention is of such a scale that it would flow within the desicated tubules by capillary action, that the biopolymer or chitosan would bind to bacteria within the dentinal tubules, that the components would act to kill the bacteria and seal the dentinal tubules, that the fluoride would form fluorapatite when binding with the tooth. A dental restoration could be placed directly after or at a later date to seal the tooth or for cosmetic reasons.

A specific embodiment of the medical device and solution may comprise chitosan, silver nanoparticle, and silver fluoride or sodium fluoride. The chitosan may be a modified chitosan, such as an at least partially deacetylated chitosan. The silver nanoparticle may be bonded to the chitosan.

In one such embodiment, the medical device or solution comprises chitosan in a range of 10,000 ppm to 30,000 ppm, nanosilver in a range of 100 ppm to 8,000 ppm, and fluoride ions (from silver fluoride or sodium fluoride, for example) in a range of 10,000 ppm to 45,000 ppm.

In another embodiment, the medical device or solution comprises chitosan in a ratio of silver fluoride or sodium fluoride in a range of 1:1 to 15:1. In another embodiment, medical device or solution comprises chitosan in a ratio to silver fluoride or sodium fluoride in a range of between 2:1 and 20:1.

In an embodiment, the medical device or solution comprises a ratio of chitosan to nanosilver may be in a range of 30:1 to 2:1. In another embodiment, the medical device or solution comprises a ratio of chitosan to nanosilver may be in a range of 30:1 to 5:1.

Method of Occluding Dentinal Tubules

The invention is also directed to methods of occluding a dentinal tubule in a tooth. An embodiment of the method of occluding dentinal tubules in teeth comprises applying an amount of a medical device or solution as described herein to the treatment area of the at least one tooth. The medical device or solution enters the dentinal tubule by any means including, but not limited to, pressure, gravity, capillary action, for example.

The method may be performed by a medical professional such as but not limited to a dentist, a dental hygienist, a dental assistant, or other aid. The method performed by the medical professional may comprise applying the medical device or solution to at least one tooth with a brush. The brush may be a microbrush applicator or other dental applicator.

To assist in the medical device or solution in entering the dentinal tubule, the tooth may be dried prior to application of the medical device or solution. By drying the tooth, any water or other volatile liquids in the dentinal tubule are at least partially removed thereby at least partially emptying the dentinal tubule. The method may, therefore, comprise desiccating at least one dentinal tubule to form a desiccated tubule.

This provides free space for the medical device or solution to enter the dentinal tubule and will increase the capillary action within the dentinal tubule. To further assist the medical device or solution entering the dentinal tubule, the method may include applying a covering agent over the treatment area of the tooth. The covering helps the medical device or solution remain on the treatment area for a longer period of time.

Therefore, the method of occluding dentinal tubules in teeth may comprise drying a treatment area of at least one tooth, applying an amount of a medical device to the treatment area of the at least one tooth, wherein the medical device as described herein, and applying a covering agent over the treatment area of the tooth. For example, the medical device or solution may comprise a polysaccharide; an antimicrobial metal or metal ion nanoparticle bound to the low molecular weight polysaccharide to form a nanoparticle gel and an antimicrobial metal fluoride encompassed within the nanoparticle gel.

Embodiments of the method may further comprise isolating the tooth. The method of isolating the tooth may be any method known in the art. Applying the medical device or solution may be done by any means including, but not limited to, pouring, spraying, dropping, or brushing, for example. In one embodiment, the method comprises applying an effective amount the medical device or solution using a microbrush to apply a drop of the solution.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by both this disclosure. It is indeed intended that the scope of this disclosure should be determined by a proper legal interpretation and construction of the disclosure, including equivalents, as understood by those of skill in the art relying upon the complete disclosure present at the time of filing.

The invention claimed is:

1. A method of occluding dentinal tubules in teeth, comprising:
    drying at least one tooth;
    applying an amount of a medical device to the treatment area of the at least one tooth, wherein the medical device comprises:
        a solution, comprising:
            a nanoparticle comprising chitosan in a range of 10,000 ppm to 30,000 ppm;
            a nanosilver particle bound to the chitosan in a range of 100 ppm to 8,000 ppm; and
            an antimicrobial metal fluoride encompassed within the nanoparticle, wherein the metal fluoride is sodium fluoride in a concentration such that fluoride ions are present in the solution in a range of 10,000 ppm to 45,000 ppm; and
    applying a covering agent over the treatment area of the tooth.

2. The method of claim 1, further comprising isolating the tooth.

3. The method of claim 2, wherein the applying an amount of the medical device comprises using a microbrush to apply a drop of the solution.

4. The method of claim 1, wherein drying at least one tooth comprises desiccating at least one dentinal tubule to form a desiccated tubule.

5. The method of claim 4, wherein the chitosan is drawn into the desiccated tubule by capillary action.

6. The method of claim 5, wherein the chitosan binds to bacteria within the desiccated tubule.

7. The method of claim 1, wherein the medical device or solution kills the bacteria and seals the dentinal tubules.

8. The method of claim 7, wherein the antimicrobial metal fluoride forms fluorapatite when binding with the tooth.

9. The method of claim 1, wherein the chitosan has a molecular weight in the range of 50,000 to 200,000 Dalton.

\* \* \* \* \*